US008684936B2

(12) United States Patent
Specht

(10) Patent No.: US 8,684,936 B2
(45) Date of Patent: *Apr. 1, 2014

(54) METHOD AND APPARATUS TO PRODUCE ULTRASONIC IMAGES USING MULTIPLE APERTURES

(71) Applicant: Maui Imaging, Inc., Sunnyvale, CA (US)

(72) Inventor: Donald F. Specht, Los Altos, CA (US)

(73) Assignee: Maui Imaging, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/632,929

(22) Filed: Oct. 1, 2012

(65) Prior Publication Data

US 2013/0035595 A1   Feb. 7, 2013

Related U.S. Application Data

(63) Continuation of application No. 13/215,966, filed on Aug. 23, 2011, now Pat. No. 8,277,383, which is a continuation of application No. 11/865,501, filed on Oct. 1, 2007, now Pat. No. 8,007,439.

(60) Provisional application No. 60/862,951, filed on Oct. 25, 2006, provisional application No. 60/940,261, filed on May 25, 2007.

(51) Int. Cl.
  *A61B 8/14* (2006.01)

(52) U.S. Cl.
  USPC .............. 600/459; 600/437; 600/463

(58) Field of Classification Search
  USPC .............. 600/437–469; 382/128–132
  See application file for complete search history.

(56) References Cited

U.S. PATENT DOCUMENTS 4,097,835 A    6/1978 Green
4,271,842 A    6/1981 Specht et al.
(Continued)

FOREIGN PATENT DOCUMENTS

EP    2187813 A1    5/2010
EP    2198785 A1    6/2010
(Continued)

OTHER PUBLICATIONS

Specht et al.; U.S. Appl. No. 13/690,989 entitled "Motion Detection Using Ping-Based and Multiple Aperture Doppler Ultrasound," filed Nov. 30, 2012.
(Continued)

*Primary Examiner* — Sanjay Cattungal
(74) *Attorney, Agent, or Firm* — Shay Glenn LLP

(57) ABSTRACT

A combination of an ultrasonic scanner and an omnidirectional receive transducer for producing a two-dimensional image from received echoes is described. Two-dimensional images with different noise components can be constructed from the echoes received by additional transducers. These can be combined to produce images with better signal to noise ratios and lateral resolution. Also disclosed is a method based on information content to compensate for the different delays for different paths through intervening tissue is described. The disclosed techniques have broad application in medical imaging but are ideally suited to multi-aperture cardiac imaging using two or more intercostal spaces. Since lateral resolution is determined primarily by the aperture defined by the end elements, it is not necessary to fill the entire aperture with equally spaced elements. Multiple slices using these methods can be combined to form three-dimensional images.

15 Claims, 11 Drawing Sheets

(56) References Cited

U.S. PATENT DOCUMENTS

| | | |
|---|---|---|
| 4,333,474 A | 6/1982 | Nigam |
| 4,339,952 A | 7/1982 | Foster |
| 4,501,279 A | 2/1985 | Seo |
| 4,682,497 A | 7/1987 | Sasaki |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,305,756 A | 4/1994 | Entrekin et al. |
| 5,339,282 A | 8/1994 | Kuhn et al. |
| 5,355,888 A | 10/1994 | Kendall |
| 5,409,010 A | 4/1995 | Beach et al. |
| 5,442,462 A | 8/1995 | Guissin |
| 5,503,152 A | 4/1996 | Oakley et al. |
| 5,515,853 A | 5/1996 | Smith et al. |
| 5,522,393 A | 6/1996 | Phillips et al. |
| 5,558,092 A | 9/1996 | Unger et al. |
| 5,675,550 A | 10/1997 | Ekhaus |
| 5,769,079 A | 6/1998 | Hossack |
| 5,797,845 A | 8/1998 | Barabash et al. |
| 5,798,459 A | 8/1998 | Ohba et al. |
| 5,876,342 A | 3/1999 | Chen et al. |
| 5,916,169 A | 6/1999 | Hanafy et al. |
| 5,964,707 A | 10/1999 | Fenster et al. |
| 6,014,473 A | 1/2000 | Hossack et al. |
| 6,048,315 A | 4/2000 | Chiao et al. |
| 6,056,693 A | 5/2000 | Haider |
| 6,122,538 A | 9/2000 | Sliwa, Jr. et al. |
| 6,129,672 A | 10/2000 | Seward et al. |
| 6,148,095 A | 11/2000 | Prause et al. |
| 6,162,175 A | 12/2000 | Marian, Jr. et al. |
| 6,166,853 A | 12/2000 | Sapia et al. |
| 6,193,665 B1 | 2/2001 | Hall et al. |
| 6,196,739 B1 | 3/2001 | Silverbrook |
| 6,246,901 B1 | 6/2001 | Benaron |
| 6,304,684 B1 | 10/2001 | Niczyporuk et al. |
| 6,324,453 B1 | 11/2001 | Breed et al. |
| 6,361,500 B1 | 3/2002 | Masters |
| 6,394,955 B1 | 5/2002 | Perlitz |
| 6,423,002 B1 | 7/2002 | Hossack |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,517,484 B1 | 2/2003 | Wilk et al. |
| 6,543,272 B1 | 4/2003 | Vitek |
| 6,614,560 B1 | 9/2003 | Silverbrook |
| 6,652,461 B1 | 11/2003 | Levkovitz |
| 6,690,816 B2 | 2/2004 | Aylward et al. |
| 6,695,778 B2 | 2/2004 | Golland et al. |
| 6,702,745 B1 | 3/2004 | Smythe |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,843,770 B2 | 1/2005 | Sumanaweera |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,447,535 B2 | 11/2008 | Lavi |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,699,776 B2 | 4/2010 | Walker et al. |
| 7,722,541 B2 | 5/2010 | Cai |
| 7,744,532 B2 | 6/2010 | Ustuner et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,157,737 B2 | 4/2012 | Zhang et al. |
| 8,202,219 B2 | 6/2012 | Luo et al. |
| 8,277,383 B2 | 10/2012 | Specht |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0113694 A1 | 5/2005 | Haugen et al. |
| 2005/0147297 A1 | 7/2005 | McLaughlin et al. |
| 2005/0240125 A1 | 10/2005 | Makin et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0122506 A1 | 6/2006 | Davies et al. |
| 2006/0173327 A1 | 8/2006 | Kim |

(56) References Cited

U.S. PATENT DOCUMENTS

| | | |
|---|---|---|
| 2006/0262291 A1 | 11/2006 | Hess et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0161904 A1 | 7/2007 | Urbano |
| 2007/0167752 A1 | 7/2007 | Proulx et al. |
| 2007/0232914 A1 | 10/2007 | Chen et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0112095 A1 | 4/2009 | Daigle |
| 2009/0182237 A1 | 7/2009 | Angelsen et al. |
| 2009/0208080 A1 | 8/2009 | Grau et al. |
| 2009/0306510 A1 | 12/2009 | Hashiba et al. |
| 2010/0016725 A1 | 1/2010 | Thiele |
| 2010/0121193 A1 | 5/2010 | Fukukita et al. |
| 2010/0121196 A1 | 5/2010 | Hwang et al. |
| 2010/0168578 A1 | 7/2010 | Garson, Jr. et al. |
| 2010/0217124 A1 | 8/2010 | Cooley |
| 2010/0256488 A1 | 10/2010 | Kim et al. |
| 2010/0262013 A1 | 10/2010 | Smith et al. |
| 2010/0268503 A1 | 10/2010 | Specht et al. |
| 2011/0098565 A1 | 4/2011 | Masuzawa |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1 | 8/2011 | Specht et al. |
| 2012/0036934 A1 | 2/2012 | Kröning et al. |
| 2012/0057428 A1 | 3/2012 | Specht et al. |
| 2012/0095343 A1 | 4/2012 | Smith et al. |
| 2012/0095347 A1 | 4/2012 | Adam et al. |
| 2012/0116226 A1 | 5/2012 | Specht |

FOREIGN PATENT DOCUMENTS

| | | |
|---|---|---|
| EP | 1757955 B1 | 11/2010 |
| EP | 1979739 | 10/2011 |
| EP | 1840594 B1 | 6/2012 |
| JP | 05-042138 A | 2/1993 |
| JP | 08-252253 | 10/1996 |
| JP | 2001-245884 A | 9/2001 |
| WO | WO 92/18054 A1 | 10/1992 |
| WO | WO 98/00719 A2 | 1/1998 |
| WO | WO 2006/114735 A1 | 11/2006 |
| WO | WO 2007/127147 A2 | 11/2007 |

OTHER PUBLICATIONS

Brewer et al.; U.S. Appl. No. 13/730,346 entitled "M-Mode Ultrasound Imaging of Arbitrary Paths," filed Dec. 28, 2012.

Specht et al.; U.S. Appl. No. 13/773,340 entitled "Determining Material Stiffness Using Multiple Aperture Ultrasound," filed Feb. 21, 2013.

Cristianini et al.; An Introduction to Support Vector Machines; Cambridge University Press; pp. 93-111; Mar. 2000.

Feigenbaum, Harvey, M.D.; Echocardiography; Lippincott Williams & Wilkins; Philadelphia; 5th Ed.; pp. 428, 484; Feb. 1994.

Haykin, Simon; Neural Networks: A Comprehensive Foundation (2nd Ed.); Prentice Hall; pp. 156-187; Jul. 16, 1998.

Kramb et al.,.; Considerations for using phased array ultrasonics in a fully automated inspection system. Review of Quantitative Nondestructive Evaluation, vol. 23, ed. D. O. Thompson and D. E. Chimenti, pp. 817-825, (year of publication is sufficiently earlier than the effective U.S. filing date and any foreign priority date) 2004.

Ledesma-Carbayo et al.; Spatio-temporal nonrigid registration for ultrasound cardiac motion estimation; IEEE Trans. On Medical Imaging; vol. 24; No. 9; Sep. 2005.

Leotta et al.; Quantitative three-dimensional echocardiography by rapid imaging . . . ; J American Society of Echocardiography; vol. 10; No. 8; pp. 830-839; Oct. 1997.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Sakas et al.; Preprocessing and volume rendering of 3D ultrasonic data; IEEE Computer Graphics and Applications; pp. 47-54, Jul. 1995.

Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

(56) References Cited

OTHER PUBLICATIONS

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. On Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.

Wells, P.N.T.; Biomedical ultrasonics; Academic Press; London, New York, San Francisco; pp. 124-125; Mar. 1977.

Widrow et al.; Adaptive signal processing; Prentice-Hall; Englewood Cliffs, NJ; pp. 99-116; Mar. 1985.

Call et al.; U.S. Appl. No. 13/850,823 entitled "Systems and methods for improving ultrasound image quality by applying weighting factors," filed Mar. 26, 2013.

Specht et al.; U.S. Appl. No. 13/894,192 entitled "Multiple Aperture Ultrasound Array Alignment Fixture," filed May 14, 2013.

METHOD AND APPARATUS TO PRODUCE ULTRASONIC IMAGES USING MULTIPLE APERTURES

CROSS REFERENCE TO RELATED APPLICATIONS

This application is a continuation of U.S. patent application Ser. No. 13/215,966, filed Aug. 23, 2011, now U.S. Pat. No. 8,277,383; which application is a continuation of U.S. patent application Ser. No. 11/865,501, filed Oct. 1, 2007, now U.S. Pat. No. 8,007,439; which application claims the benefit of U.S. Provisional Patent Applications No. 60/862,951, filed Oct. 25, 2006, and No. 60/940,261, filed May 25, 2007; all of which are incorporated by reference in their entirety herein.

BACKGROUND OF THE INVENTION

1. Field of the Invention

The present invention relates generally to imaging techniques used in medicine, and more particularly to medical ultrasound, and still more particularly to an apparatus for producing ultrasonic images using multiple apertures.

2. Discussion of Related Art Including Information Disclosed Under 37 CFR §§1.97, 1.98

In conventional ultrasonic imaging, a focused beam of ultrasound energy is transmitted into body tissues to be examined and the returned echoes are detected and plotted to form an image. In echocardiography the beam is usually stepped in increments of angle from a center probe position, and the echoes are plotted along lines representing the paths of the transmitted beams. In abdominal ultrasonography the beam is usually stepped laterally, generating parallel beam paths, and the returned echoes are plotted along parallel lines representing these paths. The following description will relate to the angular scanning technique for echocardiography (commonly referred to as a sector scan). However, the same concept with modifications can be implemented in abdominal scanners.

The basic principles of conventional ultrasonic imaging are well described in the first chapter of Echocardiography, by Harvey Feigenbaum (Lippincott Williams & Wilkins, 5$^{th}$ ed., Philadelphia, 1993). These will not be repeated here except as necessary to illustrate the differences between the conventional techniques and the present invention.

It is well known that the average velocity v of ultrasound in human tissue is about 1540 m/sec, the range in soft tissue being 1440 to 1670 m/sec (see for example P. N. T. Wells, Biomedical Ultrasonics, Academic Press, London, New York, San Francisco, 1977). Therefore, the depth of an impedance discontinuity generating an echo can be estimated as the round-trip time for the echo multiplied by v/2, and the amplitude is plotted at that depth along a line representing the path of the beam. After this has been done for all echoes along all beam paths, an image is formed, such as the image 10 shown in FIG. 1, in which a circle has been imaged. The gaps between the scan lines are typically filled in by interpolation. One of the earliest interpolation algorithms applied to echocardiography was described in U.S. Pat. No. 4,271,842, to Specht et al.

In order to insonify the body tissues, a beam formed either by a phased array or a shaped transducer is scanned over the tissues to be examined. Traditionally, the same transducer or array is used to detect the returning echoes. This design configuration lies at the heart of one of the most significant limitations in the use of ultrasonic imaging for medical purposes; namely, poor lateral resolution. Theoretically the lateral resolution could be improved by increasing the aperture of the ultrasonic probe, but the practical problems involved with aperture size increase have kept apertures small and lateral resolution large. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use, the limitation on aperture size is not so obvious, but it is a serious limitation nevertheless. The problem is that it is difficult to keep the elements of a large aperture array in phase because the speed of ultrasound transmission varies with the type of tissue between the probe and the area of interest. According to the book by Wells (cited above), the speed varies up to plus or minus 10% within the soft tissues. When the aperture is kept small, the intervening tissue is, to a first order of approximation, all the same and any variation is ignored. When the size of the aperture is increased to improve the lateral resolution, the additional elements of a phased array may be out of phase and may actually degrade the image rather than improving it. The instant disclosure teaches methods to maintain all of the information from an extended phased array "in phase" and thus to achieve sought-after improved lateral resolution.

In the case of cardiology, it has long been thought that extending the phased array into a second or third intercostal space would improve the lateral resolution, but this idea has met with two problems. First, elements over the ribs have to be eliminated, leaving a sparsely filled array. New theory is necessary to steer the beam emanating from such an array. Second, the tissue speed variation described above, but not adequately addressed until this time, needs to be compensated. The same solution taught in this disclosure is equally applicable for multi-aperture cardiac scanning, or for extended sparsely populated apertures for scans on other parts of the body.

BRIEF SUMMARY OF THE INVENTION

The present invention solves both the problem of using more than one intercostal space and the problem of accommodating unknown phase delays from using elements spread over a large sparse aperture. The solution involves separating the insonifying probe from the imaging elements. The separation can be a physical separation or simply a separation in concept wherein some of the elements of the array can be shared for the two functions.

A single omni-directional receive element (such as a receive transducer) can gather all of the information necessary to reproduce a two-dimensional section of the body. Each time a pulse of ultrasound energy is transmitted along a particular path, the signal received by the omnidirectional probe can be recorded into a line of memory. [The terms "omni-directional probe," "omni probe" and/or "omni," are used synonymously herein to mean an omnidirectional probe.] When this is done for all of the lines in a sector scan, the memory can be used to reconstruct the image. This can be accomplished in the same time as data is being collected for the next frame.

There are numerous advantages to this approach, and these comprise the objects and advantages of the present invention. They include, among others:

The dominance of specular reflections so prominent in reconstructing images by returns to the main probe is greatly attenuated.

More than one omnidirectional probe can be used. Each one can be used to reconstruct an entire sector image but with different point spread functions. These can be combined to produce an image with a sharper point spread function.

Compensations can be made for different delays in different paths through the tissue.

Many more scan lines can be reconstructed than the number of pulses generated by the main probe. This overcomes the traditional limit of the number of scan lines by the speed of ultrasound in tissue, tissue depth of interest, and the time allowed between frames, which is typically $\frac{1}{30}^{th}$ second.

Artificial scan lines can be considered as overlapping, and each pixel on an output image can be imaged from information from more than one omni line of data. Therefore the output pixel can be averaged from multiple data, thus improving the signal-to-noise ratio.

Omnidirectional probes can be placed in multiple intercostal spaces, the suprasternal notch, the substernal window, multiple apertures along the abdomen and other parts of the body, and even on the end of a catheter. An advantage in using omnidirectional probes for catheter placement is that no steering is required of the probe.

Probes can be placed either on the image plane, off of it, or any combination. When placed away from the image plane, omni probe information can be used to narrow the thickness of the sector scanned.

There has thus been broadly outlined the more important features of the invention in order that the detailed description that follows may be better understood, and in order that the present contribution to the art may be better appreciated. Additional objects, advantages and novel features of the invention will be set forth in part in the description as follows, and in part will become apparent to those skilled in the art upon examination of the following. Furthermore, such objects, advantages and features may be learned by practice of the invention, or may be realized and attained by means of the instrumentalities and combinations particularly pointed out in the appended claims.

Still other objects and advantages of the present invention will become readily apparent to those skilled in this art from the following detailed description, which shows and describes only the preferred embodiments of the invention, simply by way of illustration of the best mode now contemplated of carrying out the invention. As will be realized, the invention is capable of modification in various obvious respects without departing from the invention. Accordingly, the drawings and description of the preferred embodiment are to be regarded as illustrative in nature, and not as restrictive.

DETAILED DESCRIPTION OF THE INVENTION

A key element of the present invention is that returned echoes in ultrasonography can be detected by a separate relatively non-directional receive transducer located away from the insonifying probe (transmit transducer), and the non-directional receive transducer can be placed in a different acoustic window from the insonifying probe. This probe will be called an omni-directional probe because it can be designed to be sensitive to a wide field of view.

If the echoes detected at the omni probe are stored separately for every pulse from the insonifying transducer, it is surprising to note that the entire two-dimensional image can be formed from the information received by the one omni. Additional copies of the image can be formed by additional omni-directional probes collecting data from the same set of insonifying pulses.

Figure 2:
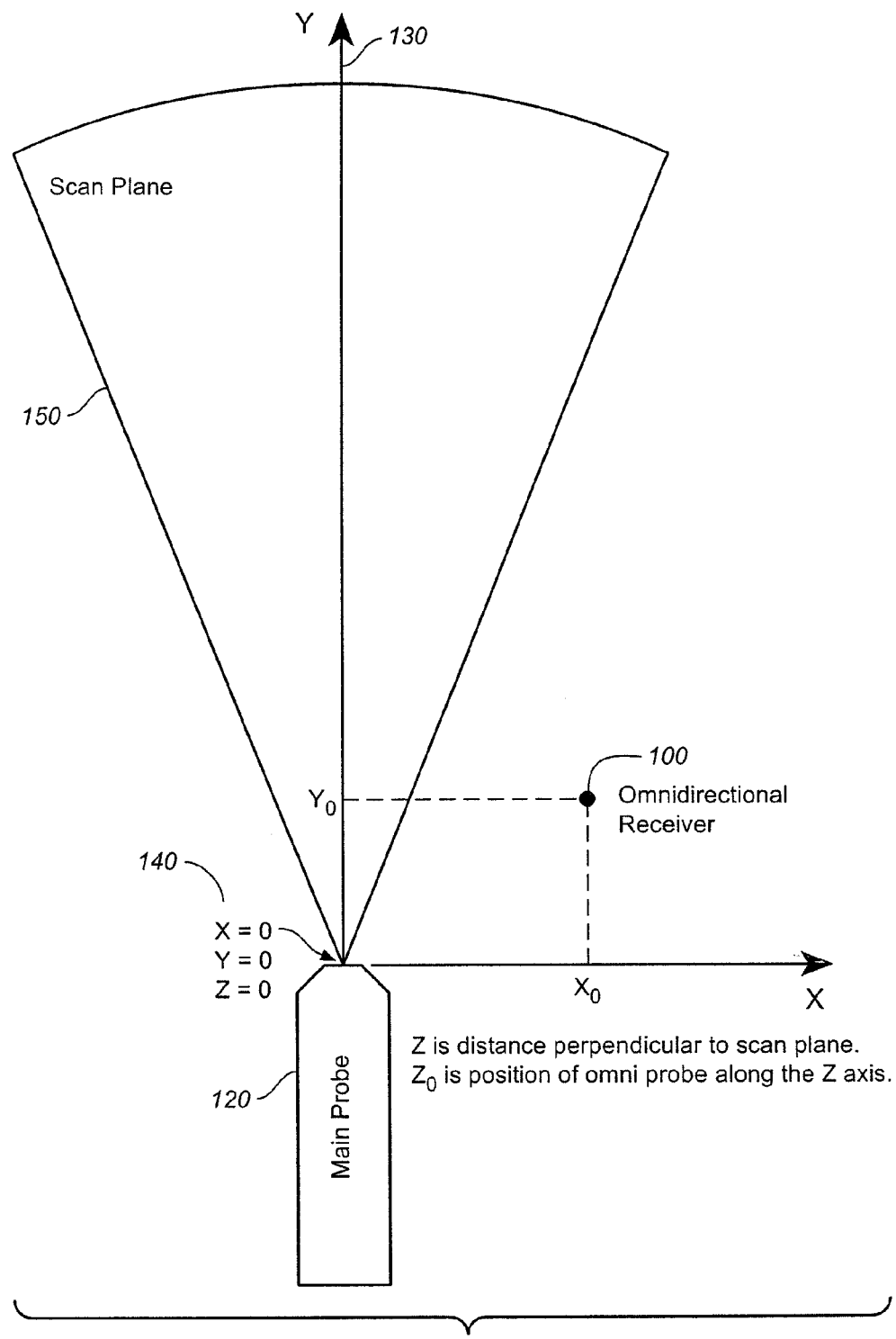
FIG. 2 is a schematic diagram of the axes representing the relative positions of the insonifying and omni-directional probes.

A large amount of straightforward computation is required to plot the amplitude of echoes received from the omni. Referring now to FIG. 2, in which there is shown the position of the omni-directional probe 100 relative to the position of the insonifying (main) probe 120 and the insonifying beam 130. The position of the omni-directional probe relative to the beam is indicated by $x_0$, $y_0$ and $z_0$ 140, where $x_0$ and $y_0$ are in the scan plane 150 scanned by the insonifying beam and $z_0$ is distance perpendicular to that plane. Instead of simply plotting the depth along the scan line $d=t\,v/2$ (where t is the round-trip time, it is now computed as that point $d=sqrt(x^2+y^2)$ for which $t\,v=d+sqrt((x-x_0)^2+(y-y_0)^2\times 2+z_0^2)$.

Figure 3:
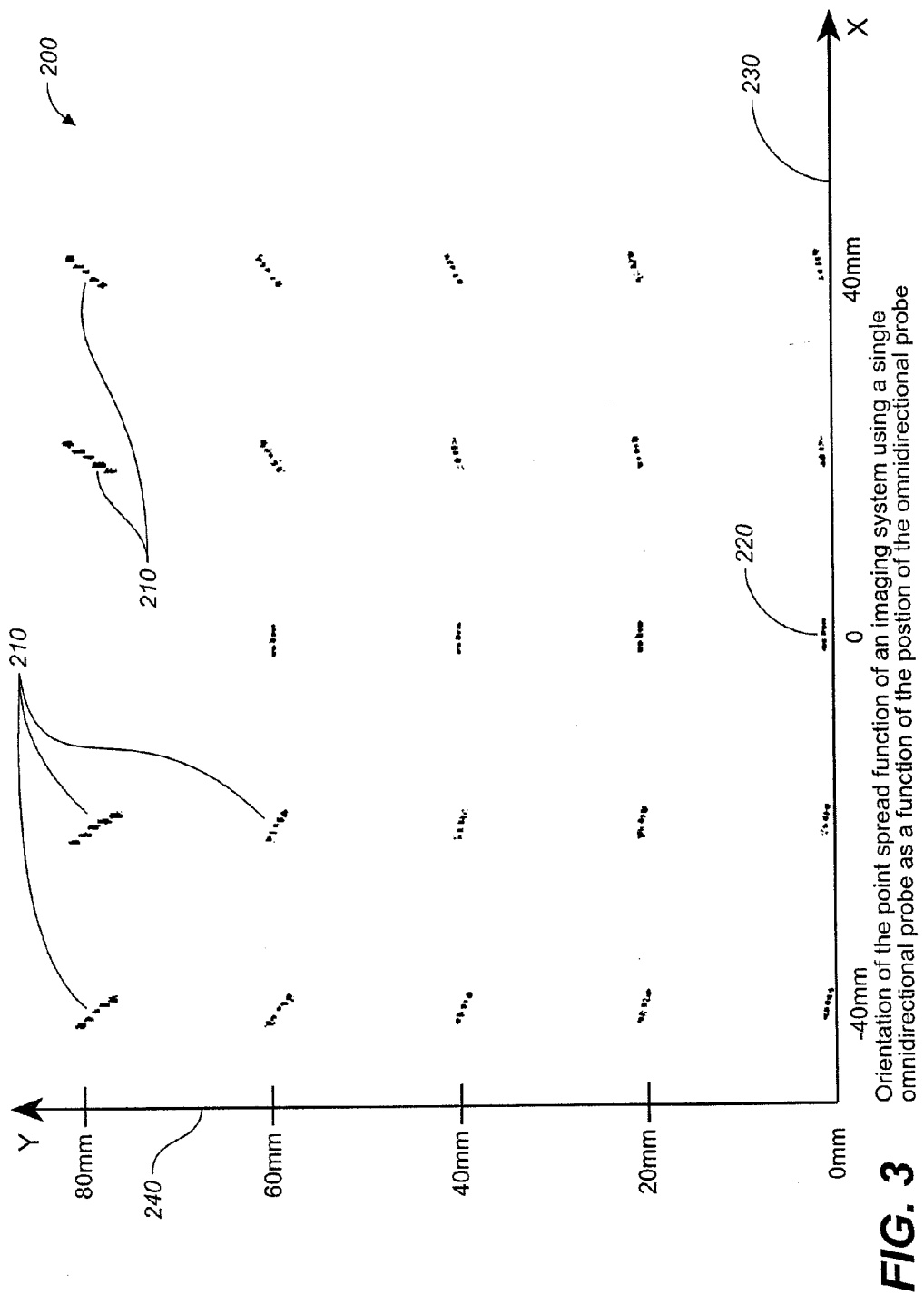
FIG. 3 is a graph showing the orientation of the point spread function of an imaging system using a single omnidirectional probe as a function of the position of the omnidirectional probe.

This procedure will produce a sector scan image similar to that using the conventional technique except that the point spread function will be rotated. FIG. 3 shows the orientation 200 of the psf as a function of the position of the omni probe. A single point at $x=0$, $y=70$ mm, $z=0$ is the point being imaged, and the groups of dots 210 each indicate the orientation of the psf if the omni-probe were placed at the location of the center of each group. The insonifying probe (main probe) is located at the center group 220 on the bottom of the figure. In this simulation the horizontal (x axis) 230 shown goes from −40 mm to +40 mm. The vertical (y axis) 240 goes from 0 to 80 mm depth.

Figure 4:
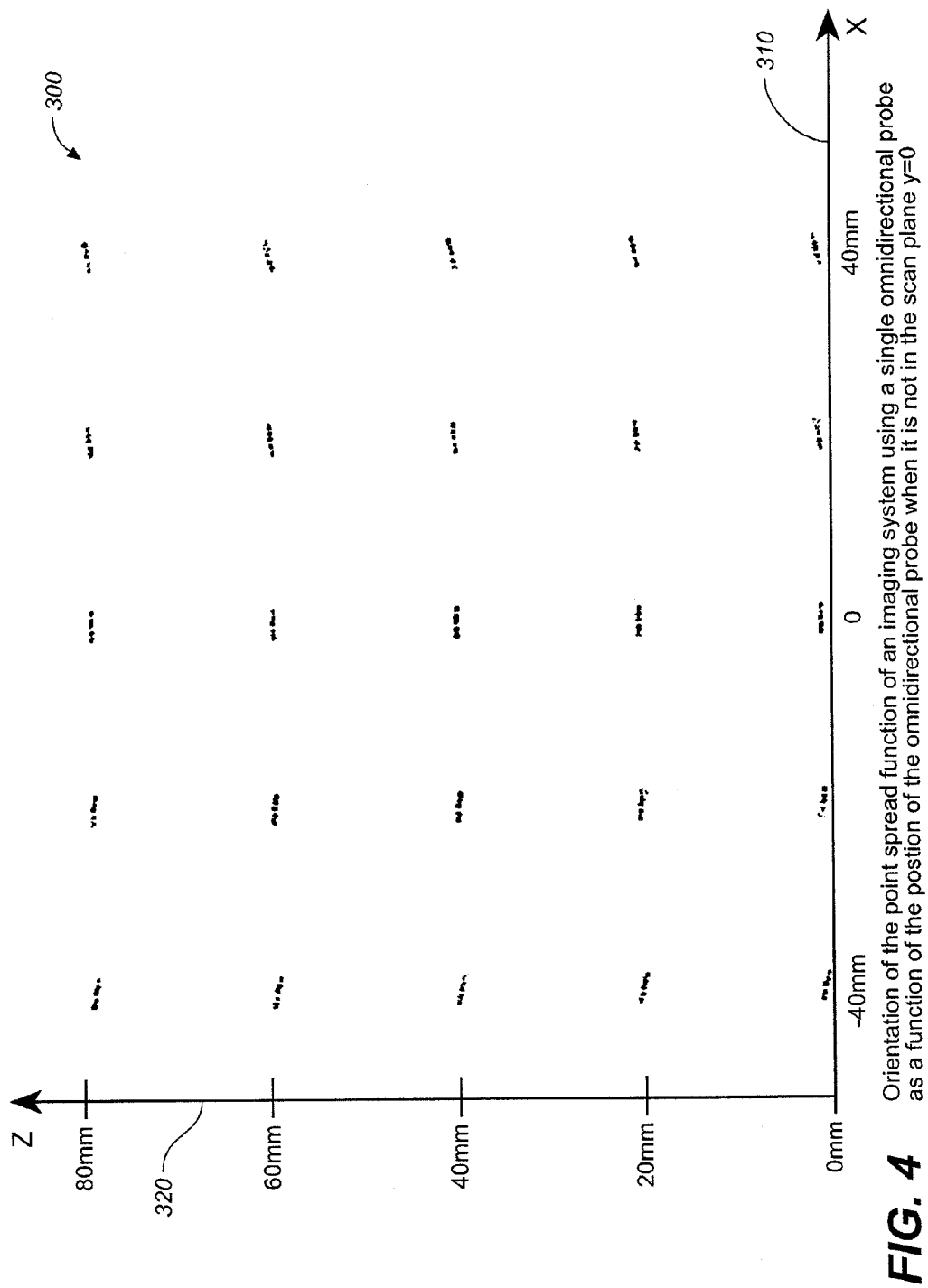
FIG. 4 is a graph showing the orientation of the point spread function of an imaging system using a single omnidirectional probe as a function of the position of the omnidirectional probe when it is not in the scan plane.

FIG. 4 shows the orientation 300 of the psf as a function of the position of the omni probe if it is not in the scan plane. In this simulation the horizontal (x axis) 310 shown again goes from −40 mm to +40 mm, but the vertical axis 320 is the z axis (distance away from the scan plane) and goes from 0 to 80 mm away from the scan plane.

Figure 5:
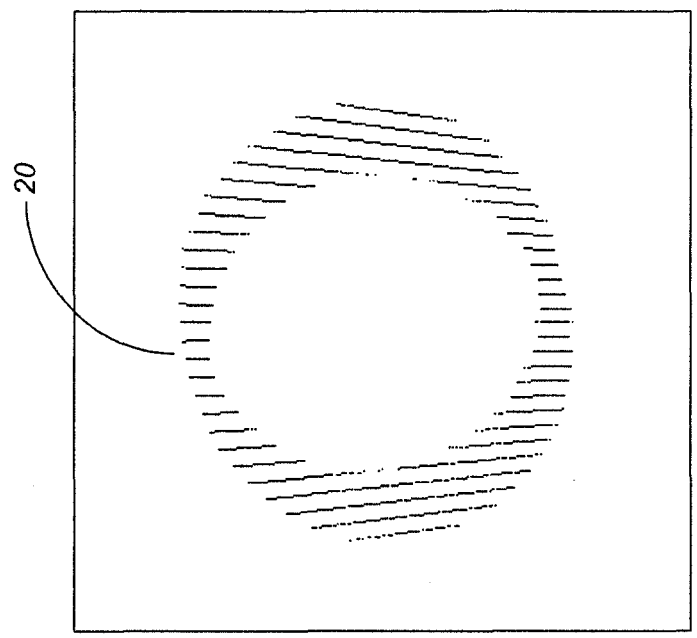
FIG. 5 is a diagrammatic view of a simulation showing the same circular object of FIG. 1 imaged by data received by a single omni element located at $x_0=40$ mm, $y_0=0$ mm, $z_0=0$ mm.
Figure 1:
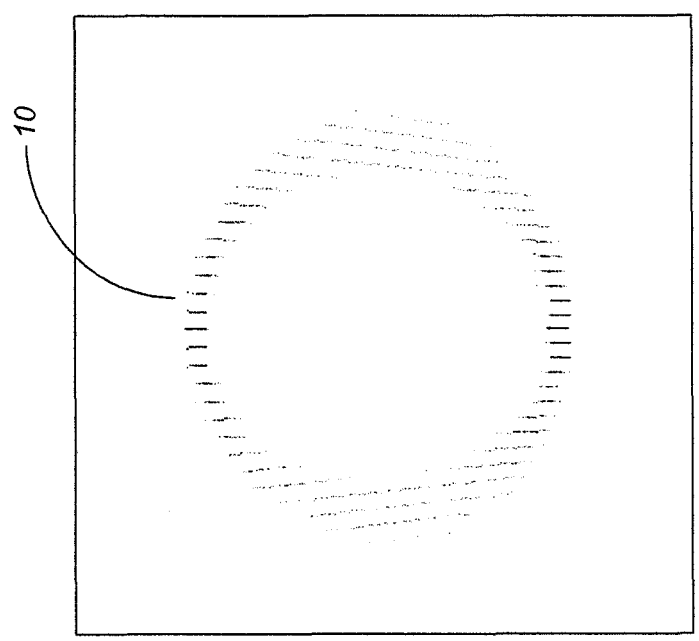
FIG. 1 is a diagrammatic view of a simulation showing a circular object imaged by a conventional sector scanner.

FIG. 5 shows a plot of the same circular object 20 as in FIG. 1, plotted, however, from data received by a single omni element. Other complete two dimensional reconstructions may be formed using data from additional omni elements, if desired.

Specular reflection is reduced using the omni probe compared to using the main probe for both insonification and detection. This is because all parts of a surface normal to the main beam are insonified with the same phase. When the phase is such that maximum echo is returned, all the echoes add to produce a specular echo. When the signals are normalized to accommodate the dynamic response of a particular display device, non-specular echoes will tend to drop out.

Figure 6:
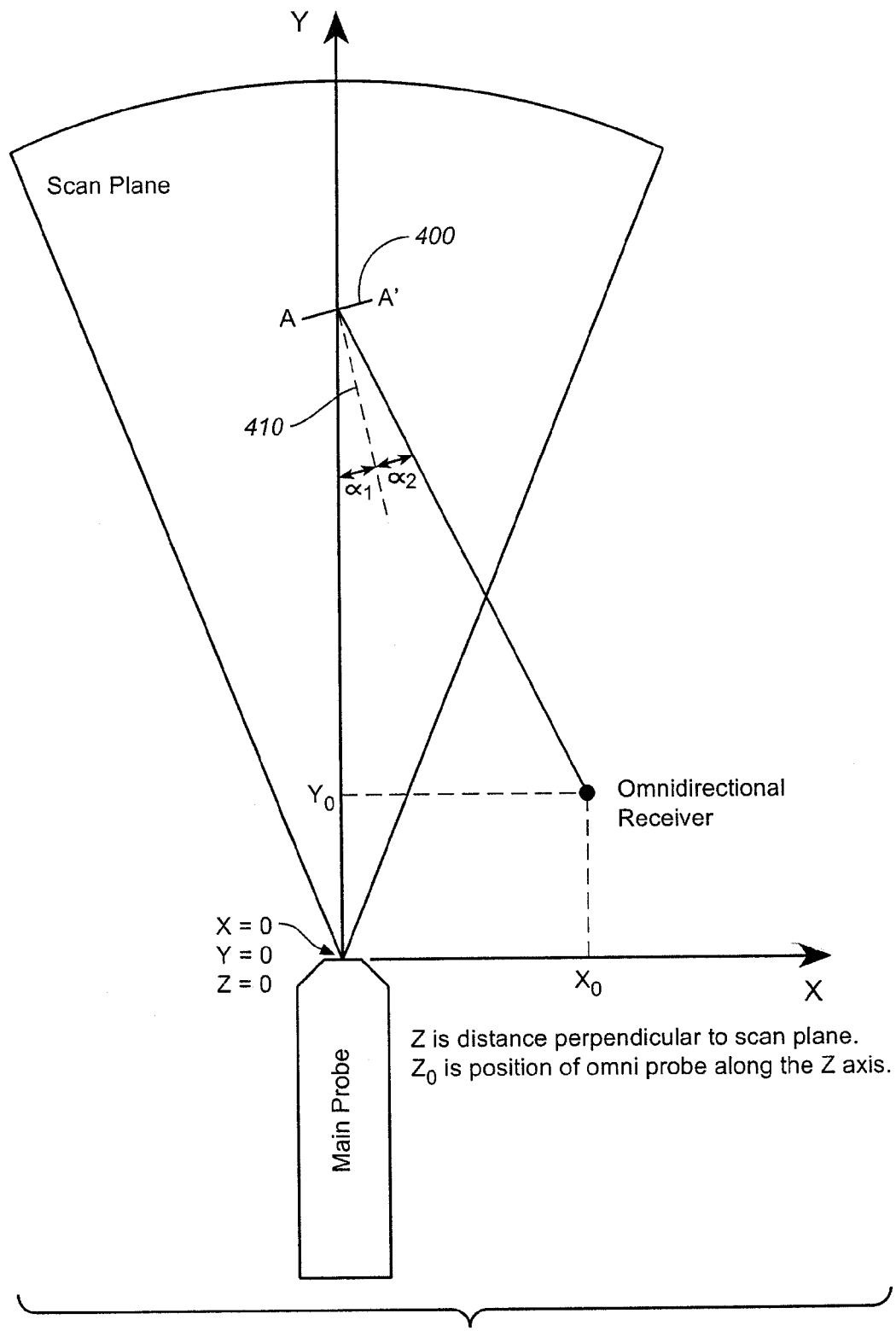
FIG. 6 is a schematic diagram illustrating the relative positions of probes showing, in addition, points A-A', which have equal round trip distances and times.

In contrast to this, and referring now to FIG. 6, there is also shown the relative positions of probes, but there is also shown points A-A' 400, which have equal round trip distances and times. Points A-A' are on a surface normal to the bisector line $a_1=a_2$ 410, which also have equal round trip distances and times, are not insonified with the same phase, and do not all reflect equally. This attenuation of the specular reflection is particularly important when visualizing circular structures which frequently have surfaces normal to the main beam.

An algorithm to plot this data on a rectangular grid is: (a) for each point on the x,y grid, convert x,y to depth and angle; (b) then find closest angle k scanned by the insonifying beam; (c) if it is sufficiently close, then convert x,y to distance to the omni; (d) compute time t=(distance to insonifying beam+distance to omni)/v; and (e) plot amplitude recorded by the omni for the k scan at x,y.

However, more information is available and should be used. It is possible to use the same technique to plot additional scan lines which were not explicitly insonified by the insonifying probe. Because of the inherently wide beam width of medical ultrasonic probes, much tissue between intentional scan lines is also insonified and returns echoes. Making use of this information is particularly important when capturing motion (especially in echocardiography) because the number of pulses that can be generated is strictly limited by the speed of ultrasound in tissue and the scan repetition rate desired.

The reconstructed image will get better as the angle between the main beam and the omni gets larger. However it is not necessary to focus a narrow beam on every element of tissue to be imaged as is true if the data is not stored and then processed before display. The lateral resolution can be reconstructed using a Wiener filter to be much better than the beam width if the noise spectrum is low enough. In one simulation of 2 circles of diameter 2.2 mm and 4.0 mm, both imaged well enough that the center was clear even though the beam width was 4.4 mm tapered from 1 to 0 by a cosine function. The Wiener filter is described in the next section.

There are four main sources of noise in ultrasonic imaging: (1) blur due to array size not wide enough; (2) shot noise; (3) reverberation from big interfaces; and (4) speckle.

Multiple probes give independent measures of shot noise, but using closely spaced elements in the main probe (if it is a phased array) will not give independent noise for the other three sources. Adding one or more omni probes will change the look angle, which will thereby change the speckle pattern and the reverberation pattern. These can be averaged out to lower the noise power spectrum. The Wiener filter can then be employed to cancel the blur.

Another way to eliminate speckle is to obtain a good sample of it for estimates of the noise spectrum to then be used in the Wiener filter.

De-blurring and de-noising by these techniques using only an external omni probe or probes will make it possible to visualize small and moving objects such as the coronary arteries. In such a case medical personnel could assess the degree of opening in the lumen or patency of bypass grafts without resort to invasive catheterization techniques.

When combining more than one image such as one from the main probe and another from one or more omni probes for the purpose of averaging out the various sources of noise, it is necessary to compensate for the variation in ultrasound velocity through different paths. Experiments have shown that small unaccounted errors in path velocity will displace the reconstructed image in both horizontal and vertical positions. Cross correlation techniques should be used to find the displacement with one image taken as reference before addition or other combination of images.

Two possibilities exist with regard to the Wiener filter. In one, a Wiener filter can be used separately on each image and then combine them. Alternatively, one can first combine the images (yielding a more complex point spread function) and then employ Wiener filtering.

In order to perform the indicated computations, it is necessary to either measure or estimate the position ($x_0$, $y_0$, $z_0$) of the omni relative to the main probe. Exact knowledge of these positions is not required because, as we have seen, the displacement of the image from the omni probe is also affected by the variation of the velocity of ultrasound in different types of tissue. For this reason it is necessary to use cross correlation or some other matching criterion to make a final correction of the position of the omni-generated image before combining with the reference image or images.

Figure 7:
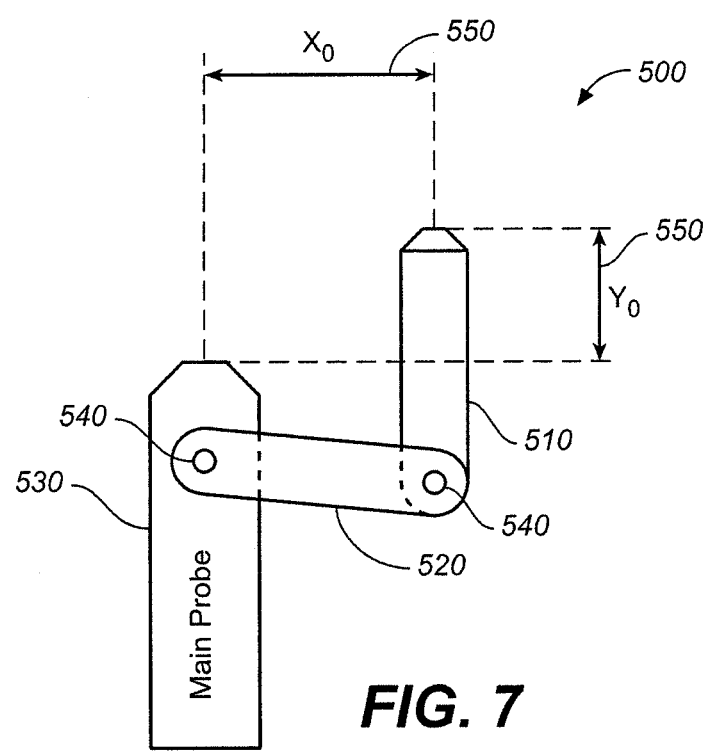
FIG. 7 is a schematic diagram showing a possible fixture for positioning an omni-directional probe relative to the main (insonifying) probe.

Determining the Position of the Omni Probe(s):

There are many ways to determine the position of the omni probe. Referring now to FIG. 7, one way is to provide apparatus 500 for pivotally and/or swivelingly mounting the omni probe 510 on a fixture 520 attached to the insonifying probe 530. The fixture preferably includes articulated joints 540 with sensors (not shown) to measure angles and distances 550 of the links. FIG. 7 illustrates a simplified version of such a fixture, wherein fixed hinges allow movement of only $x_0$ and $y_0$.

Another method is to have no mechanical connection between the omni probe and the main probe (except wires for signals and power). Instead, the omni probe can transmit a signal using radio frequencies, light, or a different frequency ultrasound to triangulation receivers mounted on the main probe or a separate platform.

A third method again has no mechanical connection between the omni probe and main probe. For this method the omni probe (or probes) can be attached to the patient with tape, and the ultrasonographer can manipulate the main probe to find the best image without regard to positioning the omni probe(s). As indicated in FIG. 4, a two-dimensional image can be formed separately from the echoes received from the omni probe and from the main probe. By adjusting four variables ($x_0$, $y_0$, $z_0$ and D, the average difference in time for ultrasound to go through different tissue types instead of traveling though idealized tissue of constant ultrasound velocity), the images can be made to coincide. The four variables can be adjusted iteratively to maximize cross-correlation or another measure of similarity. Standard multi-dimensional search techniques that could be used include gradient ascent, second order (Newton's method), simulated annealing, and genetic algorithms. A fifth variable, the angle of the psf which is necessary for deconvolution, is implied from the first four variables. Misregistration of the images can be caused by inaccurate estimation of any of the four variables, but good registration can be achieved by simply adjusting D which will tend to compensate for errors in estimates of the others.

When the application requires the highest resolution compatible with capturing motion at a high frame rate, the four variables can be estimated over several frames of information. When the ultrasonographer has selected a good view angle, the frames can be combined at high rate holding $x_0$, $y_0$, $z_0$ and D constant.

When the application requires the highest possible resolution, data can be captured (perhaps with EKG gating to capture separate images at systole and diastole) and the multi-dimensional search to optimize matching can be done more accurately although not in real time. Two advantages of this approach is that different values of D can be found for systole and diastole, and that different psfs can be used for deconvolution at different depths in the image.

Determining the Position of the Omni Probe(s) Using Correlation of the Scan Line Data Rather than Complete 2D Sectors:

A fourth method for determining the position of the omni probe(s) entails replacing the omni probe or probes with a "semi-omni probe" or probes. The reason for this is to increase the signal to noise ratio by restricting the sensitive region of the receive transducer to a plane rather than a hemisphere. Because of this restriction it is necessary to have a mechanical linkage to ensure that both the transmit and receive transducers are focused on the same plane.

Two probes could be placed in any two acoustic windows. In the case of echocardiography, one would likely be in the normal parasternal window which typically gives the clearest view of the whole heart. A second window available in most patients is the apical view. Another window usually available is the subcostal. The two probes could even be placed on either side of the sternum or in parasternal windows in two intercostal spaces.

One probe could be the standard phased array cardiac probe. The second (and third, etc.) would be used as receive only. Theoretically it could be omnidirectional, but that would necessarily provide lower signals and therefore low signal to noise ratios (S/N). A better alternative is to use a probe which is ground to be sensitive to a plane of scan but omnidirectional within that plane. A single piece of PZT would work well, but to minimize the amount of new design required it is also possible to use a second probe head similar to the main probe and then use individual elements or small groups combined to act as single elements. The design goal is to use as many elements as possible to maximize signal to noise ratio while using few enough to minimize angle sensitivity.

Figure 8:
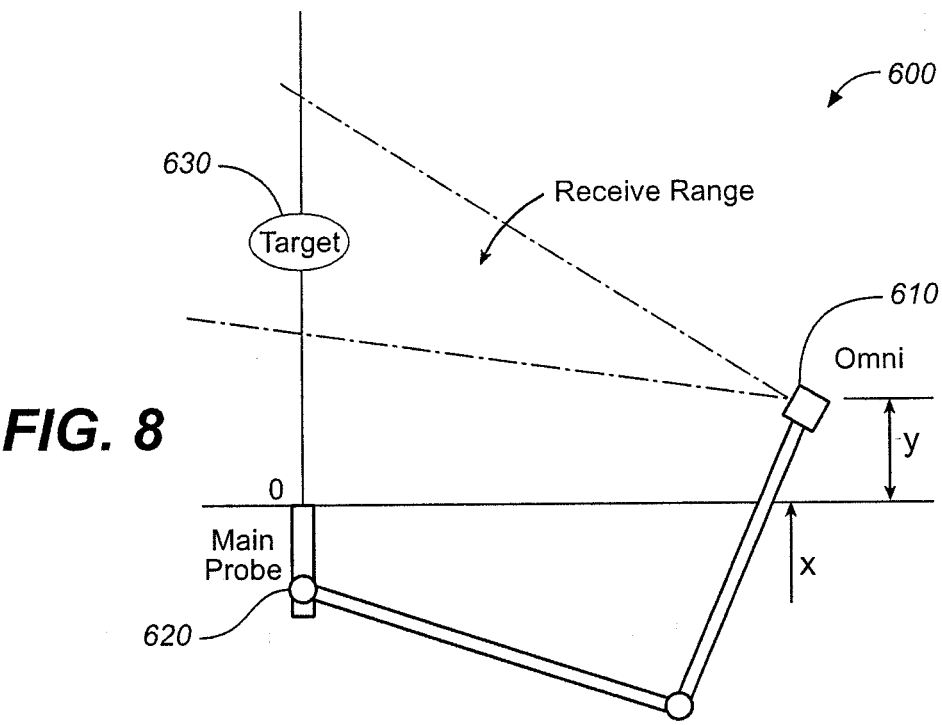
FIG. 8 is a schematic diagram showing a non-instrumented linkage for two probes.

In this embodiment 600 (see FIG. 8), the two probes 610, 620, may be linked together with an articulating mechanical linkage, which ensures that the plane of scan of each probe includes the other, but the distance between them is unconstrained. A slave servomechanism is also possible, but the mechanical linkage will be described here.

The procedure is to aim the main probe 620 at the target 630 (e.g., heart) and position the secondary probe 610 at a second window with maximum received signal strength. One possibility is that the main probe be positioned for a long axis view with the secondary probe over the apex of the heart. Some slight deviation of the long axis view may be necessary in order to maintain the secondary probe in its most sensitive spot.

The secondary probe would now be held on the patient with a mechanical housing which allows a fan or rocking motion. The disadvantage of having two probes in fixed positions on the body is that the plane of scan must include these two points. The only degree of freedom is the angle at which the scan plane enters the patient's body. For a conventional 2D examination this is a severe limitation, but if the goal is to gather three-dimensional information, this is not a limitation. The 3D information is obtained by rocking the main probe back and forth through a sufficient angle so that the entire heart is insonified. The secondary probe also rocks back and forth by virtue of the mechanical linage between the probes. The instantaneous angle of rocking must be monitored—perhaps by reference to a gyroscope mounted with the main probe. The rocking could be actuated by the hand motion of the ultrasound technician, or it could be motorized for a more-uniform angle rate. In an alternative preferred embodiment (for echocardiography), the main probe and an array of omni probes are placed in adjacent intercostal spaces using a mechanism as shown in FIG. 12.

Computer software could be provided such that the 2D slices would fill a 3D volume of voxels. After adjacent voxels are filled through interpolation, 3D information can be displayed as projections or as slices through the volume at arbitrary orientations.

The need for and one important use of the 3D information is covered in co-pending U.S. patent application Ser. No. 11/532,013, also by the present inventor, and which application is incorporated in its entirety by reference herein.

Yet another variation on this theme is to have the secondary transducer mechanically linked to the primary so that each plane of scan contains the other transducer (as above), but allow rotation of the main probe about its own axis. In this case the secondary probe would be allowed to move on the patient's body (properly prepared with ultrasound gel). It would have many elements, and an attached computer would scan them all to find those elements which have the strongest return signal.

Estimating Relative Probe Positions from Reflected Signals:

For image reconstruction it is essential to know the position of the secondary probe (x, y) relative to the main probe. This has to be evaluated separately for each frame of data because of the motion of the patient, technician, and/or motorized angle actuator. Since the linkage will prevent any difference in position (z) perpendicular to the scan plane, only x and y need be assessed.

Note that any tilt of the main probe will change the reference axes so that x and particularly y will change too.

When a pulse is transmitted from the main probe it insonifies a sequence of tissues in the path of the beam. The returns from the tissues will be received by both the main probe and the secondary, digitized and stored in the computer. Echoes from relatively proximate tissues will be different for the two probes, but echoes from mid- to far range will be similar. It is possible to use cross correlation to find similar small patches in the two stored returns. They will be similar except for the time delay relative to the launching of the pulse from the main probe. The time delay will be related to the offsets x and y. Values for x and y cannot be determined from one set of time delays, but can be determined by solving a set of simultaneous equations from two detected similar returns. These could be different patches of the same pulse return or from returns from differently directed main pulses.

Figure 9:
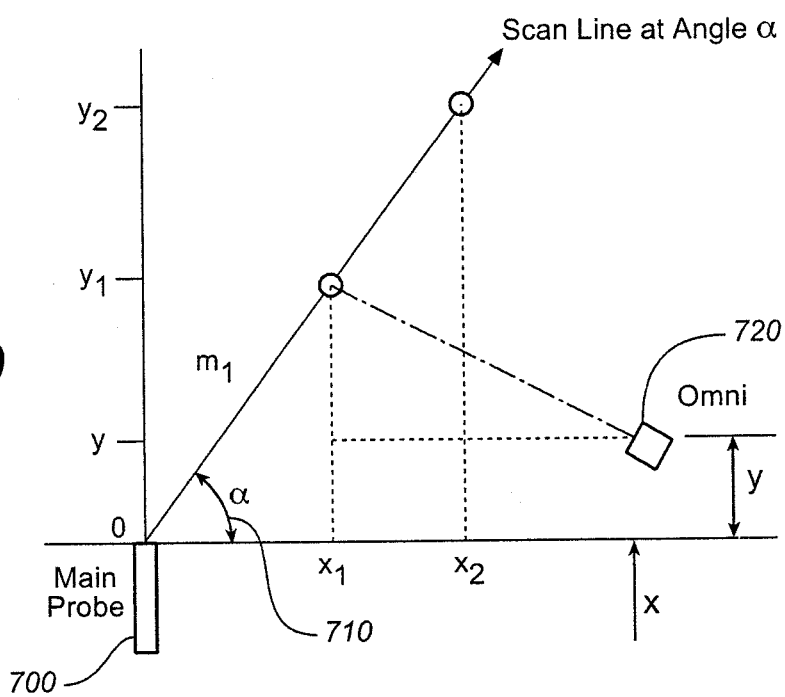
FIG. 9 is a schematic diagram showing variables for computation of x and y positions from received echoes.

Referring now to FIG. 9, if the main probe 700 transmits at angle 90°-a 710 relative to its centerline and an identifiable packet of returns occurs at time $t_{1m}$ at the main probe and at time t.sub.1s at the secondary (omni) probe 720, then:

tissue packet at $(x_1,y_1)$ is received at time $t_{1m}$, and distance $m_1=\text{sqrt}(x_1^2+y_1^2)$ tissue packet at $(x_2,y_2)$ is received at time $t_{2m}$, and distance $m_2=\text{sqrt}(x_2^2+y_2^2)$ $t_{1m}$, corresponds to time of two trips of distance $m_1$ $t_{1m}s=2m_1$, where s=speed of ultrasound in same units as m=approx. $1.54\times10^6$ mm/sec $t_{1s}s=m_1+\text{sqrt}((x_1-x)^2+(y_1-y)^2)$.

Similarly, $t_{2m}$ s=2 $m_2$ $t_{2s}s=m_2+\text{sqrt}((x_2-x)^2+(y_2-y)^2)$ $(t_{1s}s-0.5t_{1m})=(x_1-x)^2+(y_1-y)^2$ $(t_{2s}s-0.5t_{2m}s)^2=(x_2-x)^2+(y_2-y)^2$ (1)

Since Xj, $y_{15}$ $x_2$, $y_2$ and the times are known, one can solve the last two simultaneous equations for x and y.

Similarly, if a z offset between the two probes is allowed, x, y, and z can be calculated by solving three simultaneous equations.

Many more measurements from packet pairs are available. One could make a measurement on several or every scan line (angle) as measured from the main probe. Then we would have many equations in 2 unknowns which can be used to make more-accurate estimations of the 2 unknowns. Since these are nonlinear equations, a search technique can be utilized. One way to accomplish this is to compute error squared over a grid of (x, y) points using the equation:

$$E_2 = \sum_{i=1}^{N} \left( \sqrt{(x_i - x)^2 + (y_i - y)^2} - t_{is} + 0.5t_{im}s \right)^2 \quad (2)$$

The minimum $E^2$ will indicate the minimum squared error estimate of (x, y). The search should be conducted over the expected range of x and y to save time and to avoid spurious ambiguous minima.

When the z component of the relative position is not constrained to be zero, the comparable error squared equation is:

$$E_2 = \sum_{i=1}^{N} \left( \sqrt{(x_i - x)^2 + (y_i + y)^2 + z_i - z)^2} - t_{is} + 0.5t_{im}s \right)^2$$

The minimum $E^2$ will indicate the minimum squared error estimate of (x, y, z).

If the speed of sound on the return path to the secondary (omni) transducer is different from s due to different types of tissues being traversed, the values of x and y (and z if used) will be different from the geometric values. However, use of these values in the image reconstruction algorithm will automatically compensate for the different speeds.

Obviously, the probes that have been described for imaging the heart would work equally well for imaging abdominal organs and other parts of the body such as legs, arms, and neck. In fact, use of receive-only transducers in conjunction with a transmit/receive probe would work better for abdominal organs because the orientation of the probe set is not limited by the intercostal spaces formed by the ribs. Whereas the locations of the acoustic windows to the heart limit the orientation of the probe to only a few orientations and it is necessary to rock the probe to gather three dimensional data, the probes can be used on the abdomen in any orientation presently used. Therefore the probes can be used for real-time 2D scans to duplicate presently accepted procedures except with much higher lateral resolution. In fact, this application of the technology may be as important as the application to cardiology (which was our original motivation).

For abdominal scanning it is not necessary to have an elaborate spacing adjustment between the active transmit/receive elements and the receive-only elements. In fact they could all be mounted together in one rigid probe, either as a linear array or an array with known curvature. Some prior art wide linear arrays exist which insonify tissue by using a small subset of the total number of elements to transmit and receive a beam perpendicular to the array. Then another partially overlapping subset of elements is used to transmit and receive another line parallel to the first one, and so on until an entire scan is completed.

However, the same array could be partitioned into an active section plus one or more passive sections where all sections would be used for each pulse. The active section of elements would be used in transmit as a sector scanner sending out beams in a sequence of angular paths. On receive, all elements would be treated as independent relatively nondirectional receivers and their outputs would be combined to form a high resolution image by the methods taught in this patent. Cross-correlation image matching to account for the variations in ultrasound speeds could be done separately for each receive element or for groups of elements for which the speed corrections would be nearly the same.

The concept of mounting the active and receive-only elements on a rigid structure eliminates the necessity for articulating and instrumenting the spacing between elements thus making practical combined probes to be used for trans-esophageal (TEE), trans-vaginal, and trans-rectal imaging.

A final class of probes would involve putting a receive-only transducer or transducers on the end of a catheter to be inserted in an artery, vein, or urethra while a separated transmit transducer array is applied to the surface of the skin. The advantage of this approach is that the catheter could be positioned close to an organ of interest thereby reducing the total transit distance from the transmit transducer to the receive element and thus higher frequencies could be used for better resolution. The receive element(s) on the catheter would not have to be steered as it (they) would be relatively omnidirectional.

The Wiener Filter:

The Wiener filter itself is not new, but since it is important for the de-convolution step it will be described briefly here in the context of the present invention. The Wiener filter is the mean squared error optimal stationary linear filter for images degraded by additive noise and blurring. Wiener filters are usually applied in the frequency domain. Given a degraded image I(n.m.), one takes the discrete Fourier Transform (DFT) or the Fast Fourier Transform (FFT) to obtain I(u,v). The true image spectrum is estimated by taking the product of I(u,v) with the Wiener filter G(u,v):

$$\hat{S} = G(u,v)I(u,v)$$

The inverse DFT or FFT is then used to obtain the image estimate s(n,m) from its spectrum. The Wiener filter is defined in terms of the following spectra:

(a) H(u,v)—Fourier transform of the point spread function (psf);

(b) $P_s(u,v)$—Power spectrum of the signal process, obtained by taking the Fourier transform of the signal autocorrelation;

(c) $P_n(u,v)$—Power spectrum of the noise process, obtained by taking the Fourier transform of the noise auto correlation;

The Wiener filter is:

$$G(u,v) = \frac{H^*(u,v)P_S(u,v)}{|H(u,v)|^2 P_S(u,v) + P_n(u,v)}$$

The ratio $P_s/P_n$ can be interpreted as signal-to-noise ratio. At frequencies with high signal to noise ratio, the Wiener filter becomes $H^{-1}(u,v)$, the inverse filter for the psf. At frequencies for which the signal to noise ratio is low, the Wiener filter tends to 0 and blocks them out.

$P_s(u,v)+P_n(u,v)=|I(u,v)|^2$. The right hand function is easy to compute from the Fourier transform of the observed data. $P_n(u,v)$ is often assumed to be constant over (u,v). It is then subtracted from the total to yield $P_s(u,v)$.

The psf can be measured by observing a wire phantom in a tank using the ultrasound instrument. The Fourier transform of the psf can then be stored for later use in the Wiener filter when examining patients.

Because the psf is not constant as a function of range, the Wiener filter will have to be applied separately for several range zones and the resulting images will have to be pieced together to form one image for display. A useful compromise might be to optimize the Wiener filter just for the range of the object of interest such as a coronary artery or valve. It will be necessary to store separate Wiener filters for each omnidirectional probe and for the main probe when it is used as a receive transducer.

An alternative to the Wiener Filter for deconvolution is the least mean square (LMS) adaptive filter described in co-pending U.S. patent application Ser. No. 11/532,013. LMS Filtering is used in the spatial domain rather than the frequency domain, and can be applied to the radial scan line data, the lateral data at each depth, or both together.

Image sharpening can be accomplished by the use of unsharp masking. Because aperture blur is much more pronounced in the lateral dimension perpendicular to the insonifying beam) than in the radial dimension, it is necessary to perform unsharp masking in only one dimension. When using a sector scanner, this masking should be performed before scan conversion. When using a linear phased array, the unsharp masking should be performed on each data set of constant range. Unsharp masking consists of intentionally blurring an image, subtracting the result from the original image, multiplying the difference by an arbitrary factor, and adding this to the original image. In one dimension this is the same as blurring a line of data, subtracting it from the original line, and adding a multiple of the difference to the original line.

Multiple Active Transducers—Two Alternative Approaches:

It is possible to use more than one active transducer placed at multiple acoustic windows in order to achieve the same goals of increased lateral resolution and noise suppression. A practical method of providing multiple omni probes is to use a second phased array head in a second acoustic window and then treating each element or group of elements of the second phased array as a separate omni. With this configuration of probes it would be possible to switch the functions of the two probe heads on alternate scans thereby generating images with different speckle patterns which can be averaged out.

Multiple phased array heads can also be used together so that both are active on the same scan. When two (or more) phased array transducers are placed in the same scan plane, they can be programmed with delays such that they act as a single array with a gap in the array of transducer elements. The advantages of having a gap in the array include a) achieving the lateral resolution of a wide aperture without the expense of filling in acoustic elements through the gap, and b) the gap in the probe or between probes can be fitted over ribs or the sternum. The first advantage applies equally to applications other than cardiac. The disadvantages of multiple active probes is that both the transmit and receive delays have to be recomputed for each new gap dimension and/or angular orientation of one probe relative to the others.

Figure 10A:
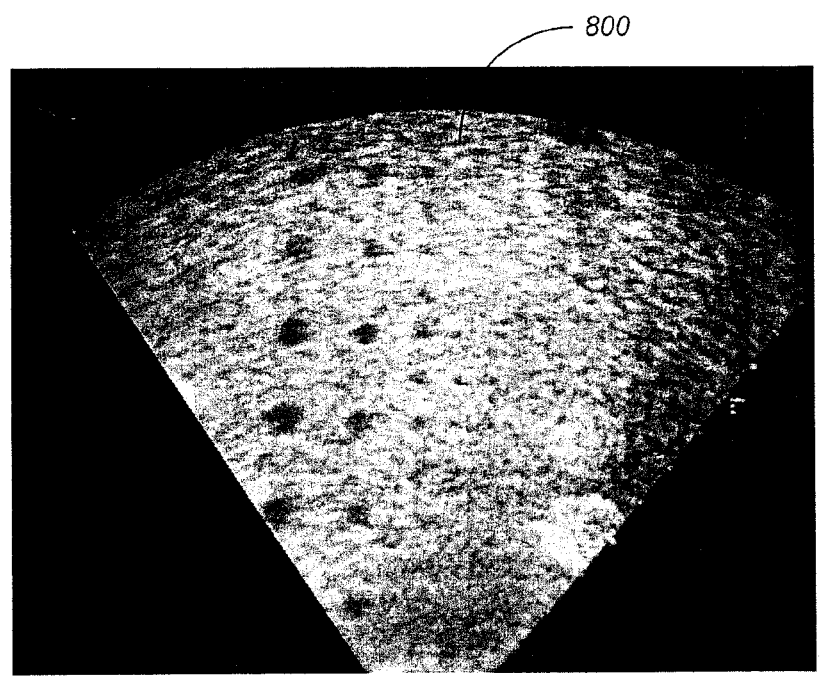
FIG. 10A is a phantom image taken with a standard Acuson 128 XP-10 with a 3.5 MHz transducer and harmonic processing.
Figure 10B:
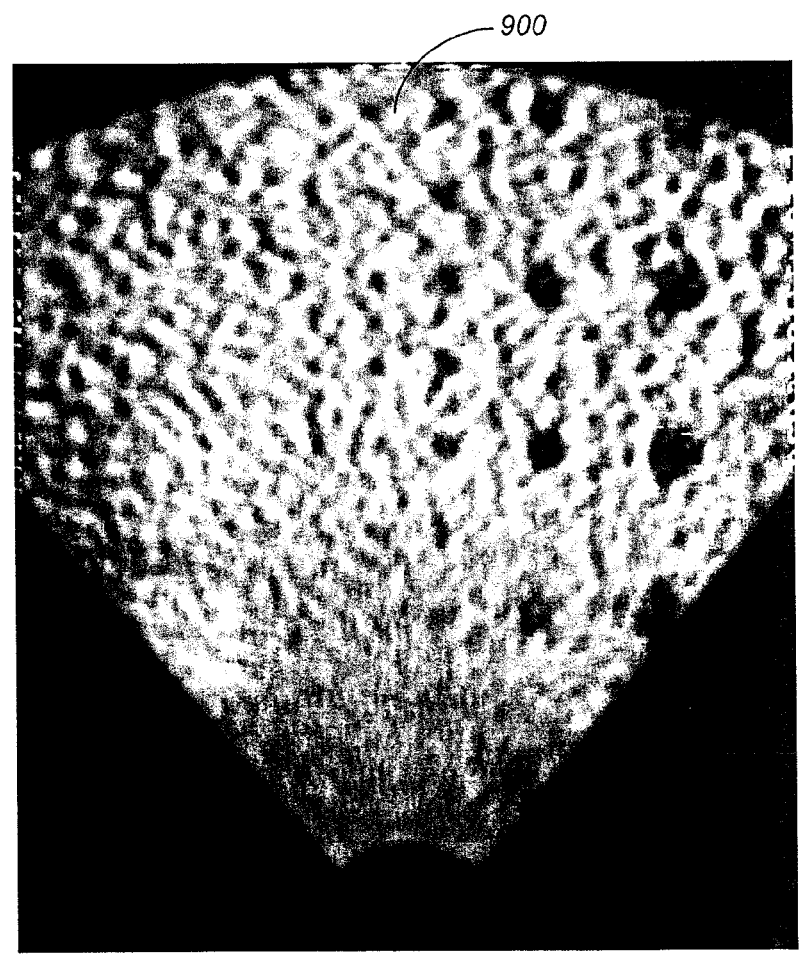
FIG. 10B is the same phantom image as that shown in FIG. 10A and taken with the same XP-10, wherein the center 64 elements were obscured but external processing employed to show improved lateral resolution. The progressions of anechoic areas on the phantom are 8 mm diameter, 6 mm, 4 mm, 3 mm, and 2 mm.

An active probe with a gap has been demonstrated to produce lateral resolution as good as the probe without the gap. This implies that larger gaps will achieve higher resolution since lateral resolution is determined primarily by the overall aperture. Referring now to FIG. 10A, there is illustrated the image 800 of an ATS Laboratories Model 539 phantom was imaged using an Acuson 128 XP-10 ultrasonic scanner with a 4V2c probe. In FIG. 10B, the same probe was used to image the phantom with its center 64 elements totally obscured by aluminum foil and electrical tape. As can be seen, the lateral resolution in the image 900 is as good as the original although the image quality is degraded by speckle and other noise.

Figure 11:
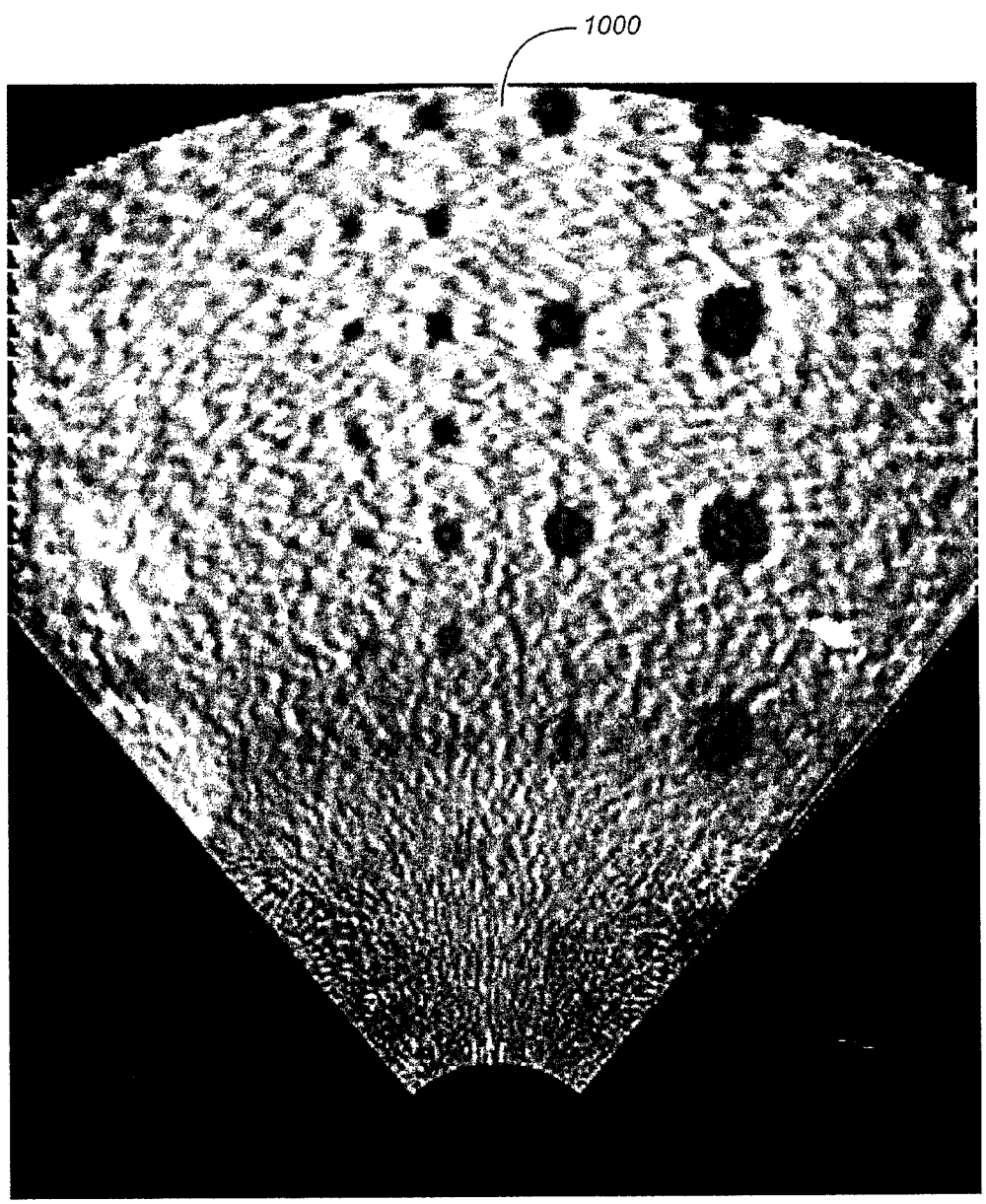
FIG. 11 is an image of the same phantom produced by the same transducer as the images in FIGS. 10A and 10B, with the center obscured, but with substantial image processing over multiple scans. Note that even though the total aperture is only 19 mm that the 2 mm diameter anechoic areas are now visible. Lateral resolution could be greatly improved if the two parts of the transducer were physically separated and the phased delays reprogrammed for the resulting geometry.

FIG. 11 shows an image 1000 of the same phantom produced by the same transducer with the center obscured, but with substantial image processing over multiple scans.

Figure 12B:
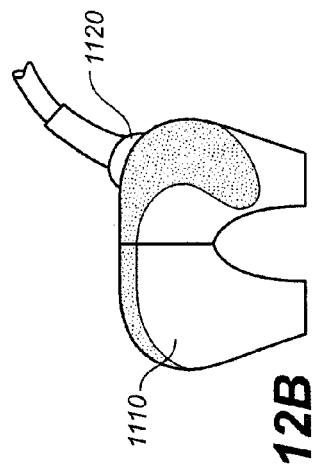
FIG. 12B is a side view in elevation thereof showing the probe in a collapsed configuration.
Figure 12C:
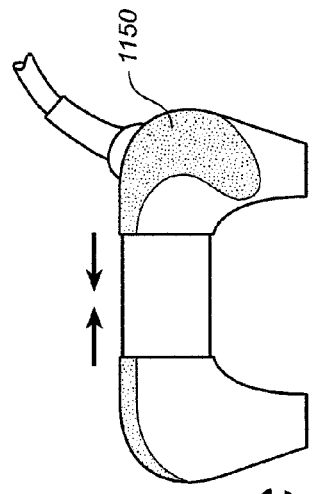
FIG. 12C shows the probe extended so as to place the heads at a maximum separation distance permitted under the probe design, and poised for pushing the separated probe apertures into a collapsed configuration.
Figure 12D:
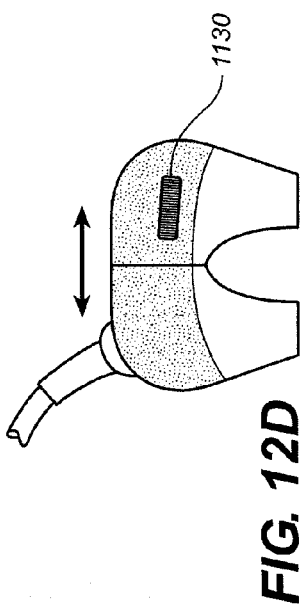
FIG. 12D is a side view in elevation again showing the probe in a collapsed configuration, with adjustment means shown (i.e., as scroll wheel).
Figure 12A:
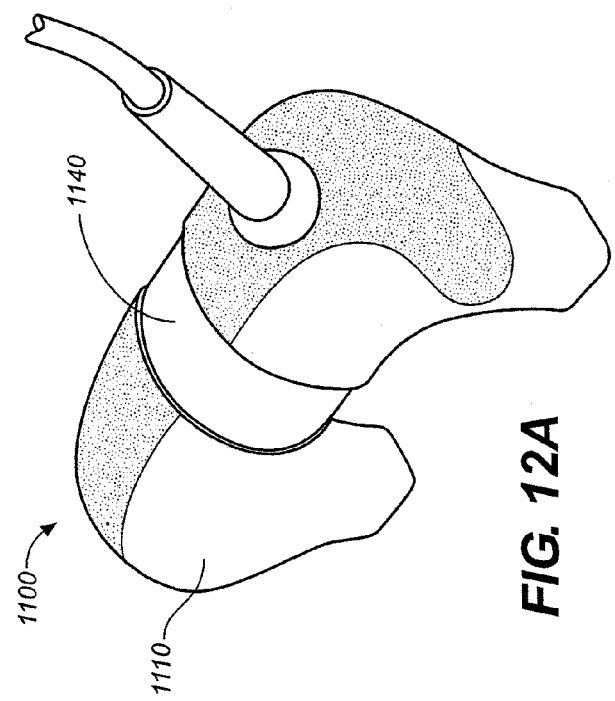
FIG. 12A is a schematic perspective view showing an adjustable, extendable hand held two-aperture probe (especially adapted for use in cardiology US imaging). This view shows the probe in a partially extended configuration.
Figure 12E:
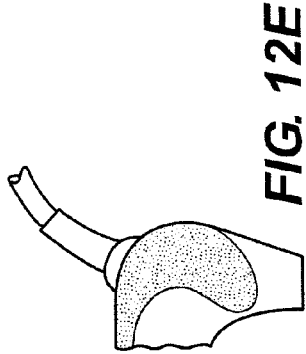
FIG. 12E is a detailed perspective view showing surface features at the gripping portion of the probe.

FIGS. 12A-E are various views showing an adjustable, extendable hand held two-aperture probe 1100 adapted for use in cardiology US imaging. This apparatus embodies the inventive concept of separating the insonifying probe 1110 (a transmit transducer) from the imaging elements 1120 (receiver transducer). This comfortable device includes adjustment means 1130, such as a scroll wheel, which selectively drives the elements either closer or further apart along either a medial telescoping portion 1140 or a medial insertable sleeve, and thereby provides a range of separation at predetermined distances. The gripping portion 1150 provides easy access to the scroll wheel and places the user's hand in the functional position to minimize overuse injury. FIG. 12A shows the probe in a partially extended configuration. FIG. 12B shows the probe in a collapsed configuration. FIG. 12C shows the probe extended so as to place the heads at a maximum separation distance permitted under the probe design. FIG. 12D shows the probe in a collapsed configuration, with adjustment means shown. And FIG. 12E is a detailed perspective view showing surface features at the gripping portion of the probe.

Figure 13:
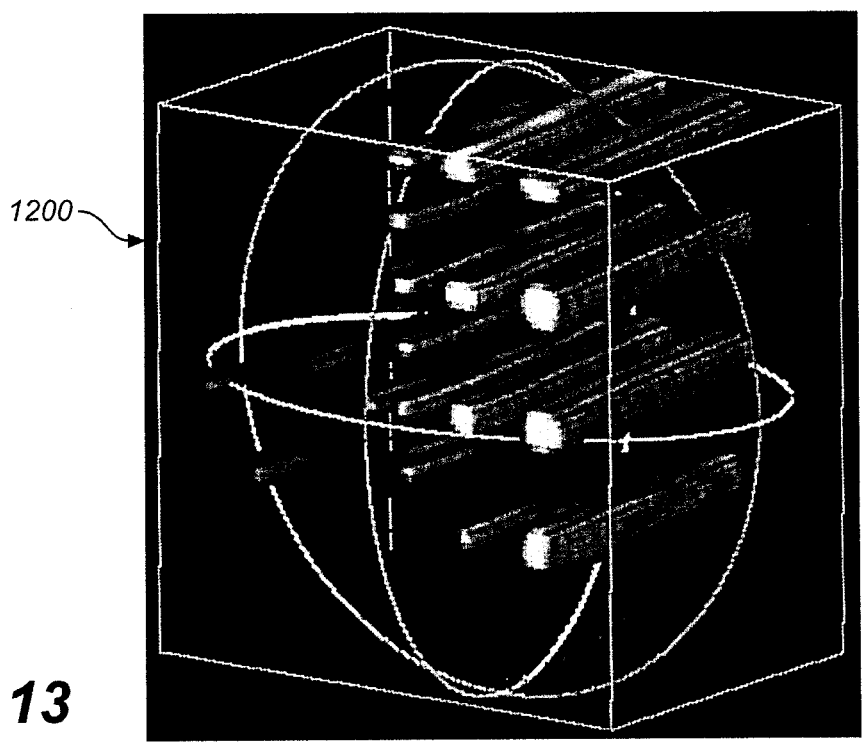
FIG. 13 is a 3D image highlighting the anechoic tubes of the ATS Model 539 phantom.

FIG. 13 shows a three-dimensional display 1200 of the anechoic tubes of the Model 539 phantom. This 3D display was formed from 13 parallel slices produced with the same transducer with the center obscured. When the total aperture is increased it will be possible to display smaller anechoic tubes such as the coronary arteries. The processing involved for this display is a combination of the techniques of the instant patent and those of co-pending U.S. patent application Ser. No. 11/532,013.

Having fully described several embodiments of the present invention, many other equivalents and alternative embodiments will be apparent to those skilled in the art. These and other equivalents and alternatives are intended to be included within the scope of the present invention.

What is claimed is:

1. An ultrasound imaging method, comprising:
    transmitting a first ultrasound pulse along a first scan line from a transmit transducer array positioned in a first acoustic window relative to a target object to be imaged;
    receiving echoes of the transmit pulse with a first omnidirectional receive transducer positioned in a second acoustic window, wherein the second acoustic window does not overlap the first acoustic window;
    storing the received echoes in a first line of computer memory;
    obtaining transducer position information defining a position and orientation of the transmit transducer array relative to the first omnidirectional receive transducer;
    retrieving the stored echoes from the first line of computer memory; and
    constructing a first image of the target object along the first scan line from the retrieved echoes and the transducer position information.

2. The method of claim 1, further comprising:
    completing a sector scan of the target object by transmitting a plurality of successive ultrasound pulses along a plurality of successive scan lines from the transmit transducer array;
    receiving echoes of each of the plurality of successive ultrasound pulses with the first omnidirectional receive transducer; and
    storing the received echoes from each of the plurality of successive ultrasound pulses in a plurality of successive lines of computer memory.

3. The method of claim 2, further comprising:
    retrieving the stored echoes from each of the plurality of successive lines of computer memory;
    constructing a plurality of images of the target object along each of the plurality of successive scan lines from the received echoes and the transducer position information; and
    combining the first image and the plurality of images along each of the plurality of successive scan lines to form a 2D image.

4. The method of claim 3, further comprising:
    receiving echoes of the transmit pulses with a second omnidirectional receive transducer positioned in a third acoustic window; and
    storing the echoes received by the second omnidirectional receive transducer in the successive lines of computer memory.

5. The method of claim 4, further comprising:
    retrieving the stored echoes received by the second omnidirectional receive transducer from the successive lines of computer memory;
    obtaining secondary transducer position information defining a position and orientation of the transmit transducer array relative to the second omnidirectional receive transducer;
    constructing a second image of the target object along the plurality of successive scan lines from the received echoes and the secondary transducer position information; and
    combining the first and second images to form a combined image.

6. The method of claim 5, further comprising, prior to combining the first and second images, adjusting at least one of the first and second images by correcting for displacement in horizontal and vertical positions.

7. The method of claim 6, further comprising applying cross-correlation techniques to correct for the displacement in horizontal and vertical positions.

8. The method of claim 4, wherein at least one of the first and second omnidirectional receive transducers comprises a single transducer element of a larger array.

9. The method of claim 4, wherein at least one of the first and second omnidirectional receive transducers comprises a group of transducer elements of a larger array.

10. The method of claim 1, wherein the target object is human tissue.

11. The method of claim 10, wherein the target object is a human heart.

12. The method of claim 11, wherein the first acoustic window is selected from the group consisting of a first parasternal intercostal space, a second parasternal intercostal space, a suprasternal notch, a substernal position, a subcostal window, an apical view, a first intercostal space adjacent the sternum, and a second intercostal space adjacent the sternum, and wherein the second acoustic window is selected from the same group.

13. The method of claim 1, further comprising plotting additional scan lines that were not explicitly insonified by the transmit transducer array.

14. The method of claim 4 wherein the second omnidirectional receive transducer comprises at least one transducer element from the transmit transducer array.

15. The method of claim 4, wherein the second omnidirectional receive transducer comprises a third transducer that is separate from the transmit transducer array and the first omnidirectional receive transducer.

* * * * *